United States Patent
Purola et al.

(10) Patent No.: US 6,897,347 B2
(45) Date of Patent: May 24, 2005

(54) FUEL COMPONENTS AND THEIR SELECTIVE MANUFACTURING METHODS

(75) Inventors: Veli-Matti Purola, Hamari (FI); Sami Toppinen, Helsinki (FI); Antti Pyhälahti, Helsinki (FI); Marina Lindblad, Helsinki (FI); Johan Grönqvist, Helsinki (FI); Pirjo Siira, Järvenpää (FI)

(73) Assignee: Fortum Oyj, Espoo (FI)

( * ) Notice: Subject to any disclaimer, the term of this patent is extended or adjusted under 35 U.S.C. 154(b) by 0 days.

(21) Appl. No.: 10/134,475

(22) Filed: Apr. 30, 2002

(65) Prior Publication Data

US 2003/0088134 A1 May 8, 2003

(30) Foreign Application Priority Data

Jul. 26, 2001 (FI) .............................................. 20011575

(51) Int. Cl.[7] ................................................ C07C 2/24
(52) U.S. Cl. ........................ 585/515; 585/511; 585/510
(58) Field of Search ............................... 585/515, 511, 585/510

(56) References Cited

U.S. PATENT DOCUMENTS

| | | | |
|---|---|---|---|
| 4,100,220 A | 7/1978 | Bowman et al. | |
| 4,356,339 A | 10/1982 | Imaizumi et al. | |
| 4,375,576 A | 3/1983 | Smith, Jr. | |
| 4,447,668 A | 5/1984 | Smith, Jr. et al. | |

FOREIGN PATENT DOCUMENTS

| | | |
|---|---|---|
| DE | 1 199 761 | 9/1965 |
| EP | 0 745 576 A1 | 12/1996 |
| FI | 982250 | 10/1998 |
| GB | 907429 | 10/1962 |
| GB | 952422 | 3/1964 |
| RU | 2137807 C1 | 9/1999 |
| WO | 01/27053 A1 | 4/2001 |
| WO | 01/79146 A1 | 10/2001 |

OTHER PUBLICATIONS

Hahn and Rohm, "Ion Exchange Resins", Dec. 1993.

*Primary Examiner*—Thuan Dinh Dang
(74) *Attorney, Agent, or Firm*—Young & Thompson

(57) ABSTRACT

The invention relates to a method for dimerizing isobutene, wherein, in dimerizing conditions, the isobutene is brought into contact with a porous cation exchange resin comprising a styrene polymer, which is cross-linked with divinyl benzene, and any sulphonic acid groups adhering to the polymer. The harmful deactivation of this catalyst, which is caused by the accumulation of the oligomers and polymers of isobutene and other $C_4$-olefins in the cation exchange resin catalyst, is essentially decreased by selecting the cation exchange resin from a group including cation exchange resins, the acid capacity of which is 4.7 equivalents/kg at a minimum, and the portion of divinyl benzene units of which is 5% by weight at a minimum and smaller than 20% by weight.

20 Claims, 4 Drawing Sheets

FUEL COMPONENTS AND THEIR SELECTIVE MANUFACTURING METHODS

The invention relates to a method for dimerizing isobutene, wherein in dimerizing conditions, the isobutene is brought into contact with a porous cation exchange resin that comprises a styrene polymer, which is cross-linked with divinyl benzene, and any sulphonic acid groups adhering to the polymer.

The invention is also related to a new use of the cation exchange resin of the above type in dimerizing isobutene.

The term "comprise" in this publication means that in addition to the components mentioned in connection with it, the product can also contain other components.

The term "styrene polymer" in this publication refers to the homopolymers of aromatic vinyl compounds of the styrene type and their derivatives, and their essential copolymers and copolymers with other monomers. The term "divinyl benzene" means both unsubstituted and substituted divinyl benzenes. See more closely the following description of the cation exchange resin.

In addition to the —$SO_3H$ group, the term "sulphonic acid group" in this publication can also refer to the —$SO_3M$ group and the compounds of these two groups, wherein M refers to some group that dissociates into cation other than hydrogen, and also the —$SO_3$ anions and ion pairs of these groups.

The method for dimerizing butene in this publication also refers to a method or a process, of which the said dimerization of isobutene forms a part only. Thus, the scope of the invention includes, among others, the etherification of isobutene (e.g., the methyl-tert-butyl-ether or the MTBE process, see publication FI 982250), wherein the dimerization in question takes place simultaneously with etherification, and the manufacturing method of isooctane, wherein the isobutene or a hydrocarbon containing it is first dimerized, in accordance with the invention, into di-isobutene and, after that, the di-isobutene is hydrogenated into isooctane.

The dimer, trimer, tetramer, oligomer, and polymer of $C_4$-olefins, such as isobutene, n-butenes, and butadiene, refer to hydrocarbon, the molecule of which is correspondingly obtained by means of the addition reaction of two, three, four, 3 to 20, and more than 20 $C_4$-olefin molecules.

The intention is to increase the octane rating of motor fuels by adding to them components with high octane ratings. MTBE, for example, is such a component, which T is obtained, when isobutene is etherified with methanol in the presence of a catalyst, which generally is an acidic cation exchange resin. The blending octane rating of MTBE-blent gasoline (RON+MON)/2 becomes about 110.

In accordance with their definition, the octane ratings RON (Research Octane Number) and MON (Motor Octane Number) are 100 for isooctane. By dimerizing isobutene into isooctene by means of a catalyst of a similar type, and by further hydrogenating it into isooctane, the octane rating of gasoline mixtures can also be improved. The most common catalyst used both in dimerizing isobutene and in its etherification is a porous cation exchange resin, which comprises a styrene polymer, which is cross-linked with divinyl benzene, and any sulphonic acid groups adhering to the polymer.

When dimerizing isobutene, it is known that heavy oligomers and polymers are generated as by-products, which gradually deactivate the catalyst. The content of linear butenes and dienes, such as butadiene, in the feed also impact on deactivation. The essential deactivating factors in such a process are as follows:

Desulphonation of the catalyst under the effect of the temperature
Decomposition of the catalyst
Oligomerizing and/or polymerizing
Neutralization of the catalyst, for example, with nitrogen compounds and metals.

From publication EP-A-745 576, a method is already known, wherein isobutene is simultaneously dimerized, and etherised with methanol into MTBE. According to the publication, dimer yield cannot be increased by means of the molar ratio of methanol and isobutene, because then the yield of harmful oligomers, mainly trimers, increases.

Application publication FI 982250 discloses a manufacturing method of isooctane, in the first stage of which the isobutene is dimerized into di-isobutene and, in the second stage; the di-isobutene is hydrogenated into isooctane. The publication suggests that the dimerizing catalyst be a styrene polymer, which is cross-linked with divinyl benzene and, after that, sulphonated with acid.

It is also known that when olefins are dimerized with ion exchange resin catalysts, molecules containing oxygen, such as methanol, MTBE, tertiary butyl alcohol (TBA) or water increase the dimer selectivity and, correspondingly, decrease the selectivity for a trimer or a tetramer. We refer to that, which is disclosed in U.S. Pat. Nos. 4,375,576, 4,447,668, and 4,100,220. Instead, prior art knows of no method, which could be used for manufacturing dimer or a mixture of dimer and ether, which are completely free of the said oligomers.

SUMMARY OF THE INVENTION

The purpose of the present invention is to eliminate or at least essentially decrease the limitations of the known technology in question, and to provide a novel solution for dimerizing isobutene, wherein the accumulation of harmful oligomer and polymer products in the catalyst is essentially reduced and the service life of the catalyst is lengthened.

In the present invention, in dimerizing conditions, isobutene is brought into contact with a porous cation exchange resin catalyst, which comprises a styrene polymer, which is cross-linked with divinyl benzene, and any sulphonic acid groups adhering to the polymer. The invention is based on the idea that the cation exchange resin for minimizing the oligomerization and the polymerization of $C_4$-olefins is selected from a group that includes cation exchange resins, the acid capacity of which is 4.7 equivalents/kg at a minimum, and the portion of divinyl benzene units of which is 5% by weight, at a minimum, and smaller than 20% by weight.

In connection with the present invention, it has namely been noticed that the most important fact that affects the deactivation of the catalyst in dimerizing isobutene is the reaction of $C_4$-olefins and their dimers into oligomers and polymers, which then reduce the activity of the catalyst. It was observed that the accumulation of oligomers and polymers in conventional dimerizing and etherification (MTBE) catalysts was intensive in dimerizing conditions of isobutene. Instead, when a cation exchange resin similar to the definition according to this application was used as a catalyst, surprisingly, hardly any oligomers and polymers accumulated in the catalyst in dimerizing conditions. Accordingly, the catalyst does not deactivate quickly, and its service life in dimerizing isobutene is lengthened, even multiplied.

The portion of divinyl benzene units of the cation exchange resin is preferably within 7–14% by weight, and most preferably about 10–12% by weight. The average diameter of the resin pores is preferably 15 nm at a minimum and smaller than 30 nm, preferably about 20–25 nm.

Figure 1:
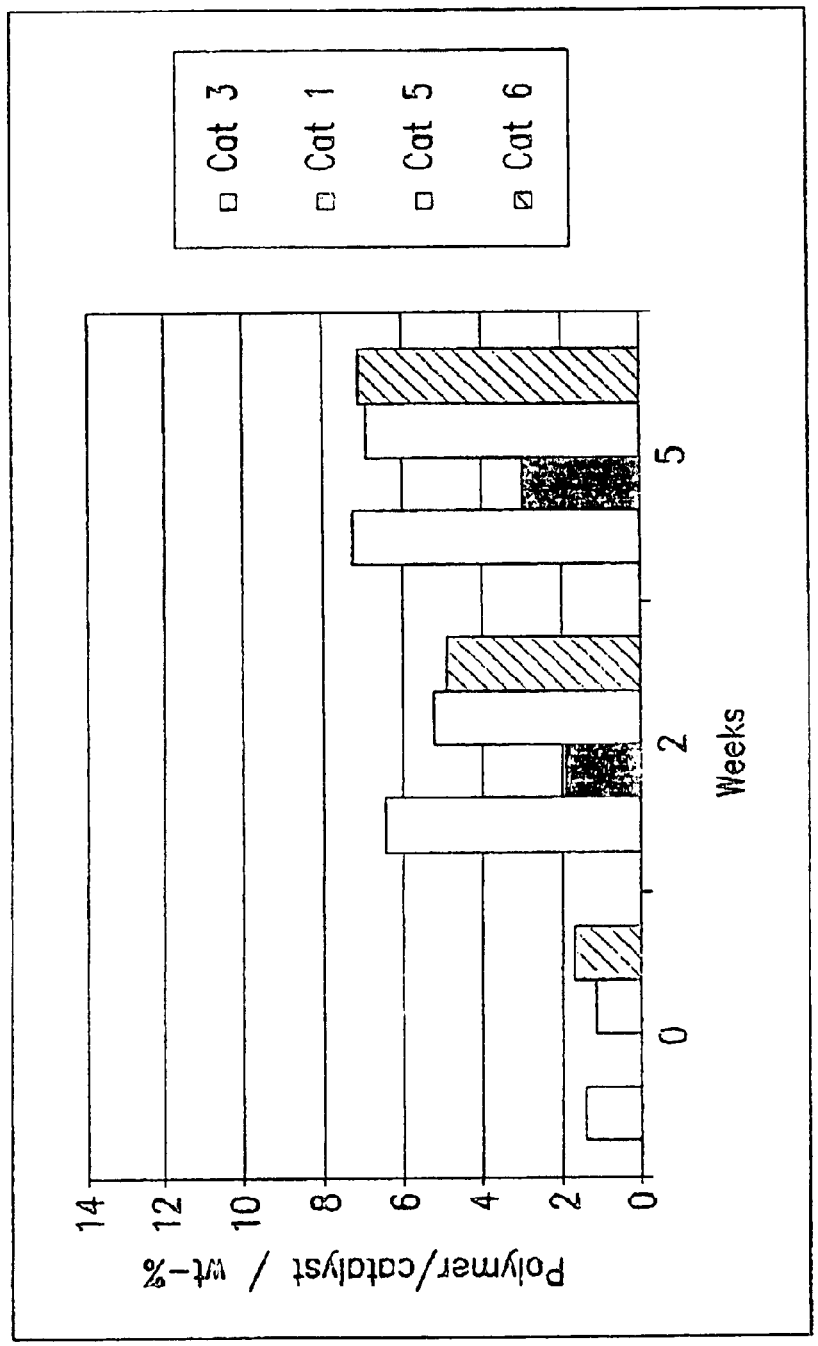
FIG. 1 shows the polymer contact as a function of the used catalyst.

It is also advantageous, if the porosity of the cation exchange resin is within 0.20–0.35 ml/g.

DETAILED DESCRIPTION OF THE INVENTION

Accordingly, the present invention uses a cation exchange resin catalyst, which comprises a styrene polymer, which is cross-linked with divinyl benzene, and any sulphonic acid groups adhering to the polymer. Typically, the resin is obtained by polymerizing (=by homopolymerization or copolymerization) aromatic vinyl compounds of the styrene type, for example, styrene, vinyl toluene, vinyl naphthalene, vinyl ethyl benzene, methyl styrene, vinyl chlorobenzene or vinyl xylene. The divinyl benzene that is used as the cross-linking monomer can be the divinyl benzene itself and/or its derivative, such as divinyl toluene or divinyl phenyl ether.

The sulphonic acid groups can be generated in the cross-linked styrene polymer by means of various methods, such as by sulphatizing styrene polymer with concentrated or fuming sulphuric acid or with chlorosulphonic acid and/or by copolymerizing styrene and divinyl benzene monomers with comonomers containing at least one sulphonic acid group.

The sulphur-containing sulphonic acid groups of the porous cation exchange resin act as active centres of the dimerization of isobutene. It was observed that good results are obtained, if the amount of sulphur in the cation exchange resin is greater than 15% by weight and smaller than 21% by weight. A preferable amount of sulphur is within 16–20% by weight.

A typical specific surface area of the cation exchange resin is within 20–45 m$^2$/g, and a preferable specific surface area is about 35 m$^2$/g. A preferable acid capacity of the active sites of the cation exchange resin is higher than about 4.7 equivalents/kg. A preferable average particle size of the cation exchange resin is within 0.6–0.85 mm.

Accordingly, the present invention uses a cation exchange resin, which is not a typical ion exchange etherification catalyst such as Amberlyst 15 or Amberlyst 35.

In the method according to the invention, isobutene can be used as such but, in practice, it is difficult to provide pure isobutene. See, among others, U.S. Pat. No. 4,447,668, which deals with the problem. Normally, isobutene is used in the form of a hydrocarbon mixture. Isobutene is preferably in the form of a hydrocarbon mixture, the isobutene content of which is 10% by weight at a minimum, preferably 20% by weight at a minimum.

The olefins in the hydrocarbon mixture are selected from the group consisting of linear 1- or 2-butene, isobutene and linear or branched C5-olefins. Alternatively, the feed can comprise a mixture of any or every of the olefins listed above. Typically, the feed comprises dimerizable components; either C4-olefins, preferably isobutene, whereby isooctene is produced, or C5-olefins, whereby substituted C10 olefins are produced. Both C4 and C5-olefins can be present in the feed, whereby a great variety of products is produced.

According to a preferred application, in which C4-hydrocarbons are dimerized, the hydrocarbon comprises a fraction obtained from isobutane dehydrogenation, when the feed comprises mainly isobutene and isobutane and possibly small amounts of C3 and C5 hydrocarbons. Typically the feed comprises 40–60 wt-% of isobutene and 60–40 wt-% isobutane, usually there is 5–20% less isobutene present than isobutane. Thus, the ratio of isobutene to isobutane is approximately 4:6 . . . 5:5.5. As an example of an isobutane dehydrogenation fraction, the following can be presented: 45 wt-% isobutene, 50 wt-% isobutane and other inert C4-hydrocarbons and approximately 5 wt-% of C3, C5- and heavier hydrocarbons altogether.

According to a second preferred application, in which C4-hydrocarbons are dimerized, the hydrocarbon comprises a C4- fraction obtained from FCC. The C4 fraction from FCC is typically composed of 10–50, in particular 10–30 wt-% isobutene, 20–70 wt-% 1-and 2-butene and approximately 5–40 wt-% butane. As an example of a typical FCC-mixture, the following can be presented: approximately 30 wt-% isobutene, approximately 17 wt-% 1-butene, approximately 33 wt-% 2-butene and approximately 20 wt-% butane. The C4 fraction is also possible to select from the group containing C4-fractions of TCC, DCC and RCC or from the C4-fraction after removal of butadiene, also called Raffinate 1 of an ethylene unit.

The following feeds are also possible: FCC gasoline, light FCC gasoline, pyrolysis C5-gasoline, TCC gasoline, RCC gasoline and Coker gasoline, typically the C5-fraction of FCC gasoline. Also isobutene prepared from chemicals can be used.

The residence time WHSV (weight hourly space velocity, unit l/h) is the amount of feed kg/h divided by the amount of dry catalyst kg. It can be 0.1–200 l/h, preferably 0.2–20 l/h. A preferable dimerization temperature of isobutene is within 50–120° C., more preferably within 80–120° C.

As already mentioned above, organic compounds that contain oxygen improve the dimerization selectivity of isobutene with respect to oligomerization. Thus, it is preferable to carry out the dimerization of isobutene in the presence of an oxygen-containing substance. When the oxygen-containing substance (oxygenate) is then fed into the process in addition to hydrocarbon, the dimer selectivity increases, whereby, correspondingly, the portion of trimers and tetramers decreases. Accordingly, the portion of dimers from the forming dimers, trimers, and tetramers of isobutene is typically 90% at a minimum. The oxygen-containing substance is either fed into the process in connection with a fresh feed or directly into the reaction zone. According to the invention, such a substance can be water, ether or alcohol, preferably $C_1$–$C_5$ alcohols (e.g., methanol, ethanol, isopropanol, tert-butanol, sec-butanol), most preferably tert-butanol. The oxygenate protects the resin catalyst by preventing it from poisoning and forming large molecules, because heavier components formed from trimers and tetramers block the resin catalyst. The optimal molar ratio of the oxygenate and isobutene in the feed the depends on the type of the feed and which oxygenate is used, but in general the molar ratio of oxygenate to isobutene should be lower than the stoichiometric ratio. E.g. in the case of tertiary butyl alcohol, the preferred ratio to isobutene is lower than 0.2.

As already mentioned, the isobutene can also be made to react with alcohol, whereby tertiary butyl ether is generated in addition to dimerization. According to one embodiment of the invention, such etherification of isobutene is effected by making the isobutene react with C1–C4 alcohols. Etherification is preferably carried out by making the isobutene react with methanol or ethanol. A preferable molar ratio between methanol/ethanol and isobutene for dimerization in connection with etherification is 0.01–1, depending on the desired proportions of other and dimer product.

As etherification takes place at a slightly lower temperature than dimerization, the temperature of the combined dimerization and etherification of isobutene is preferably within 50–70° C.

According to a first alternative, the dimerization and a possible etherification of isobutene can be carried out so that the isobutene or a hydrocarbon mixture containing it, and a possible alcohol are first fed into reaction equipment for carrying out the dimerization and possible etherification, and then the dimerization mixture is transferred into distillation equipment for separating the dimer and any possible ether.

According to a second alternative, the dimerization and possible etherification of isobutene can be carried out so that the isobutene or the hydrocarbon mixture containing it and a possible alcohol are fed into the reaction and distillation equipment for dimerization and possible etherification, and for simultaneous separation of the produced dimer and any possible ether by distillation.

In the solution according to the present invention, the reactor can be, for example, a multi-tubular reactor, wherein the tubes are filled with a catalyst. Other possible reactors include a reactor tube, a boiler reactor, a fixed bed reactor, and a fluidised bed reactor. It is preferable to use a reactor, where the catalyst is placed in several layers and cooling is provided between the layers. To optimise production, the reactors can be operated at various temperatures. The operating pressure of the reactors varies in accordance with the type of reactor and the reactor feed so that, typically, the intention is to keep the reaction mixture in a liquid phase.

Any distillation column suitable for distillation can be used as the distillation column. Such distillation columns include, for example, filling plate, valve plate, perforated plate, and bubble plate columns.

In the present invention, for the first time, a dimerization reaction of isobutene is provided, wherein no essential amounts of oligomers of $C_4$-olefins are accumulated in the catalyst. Thus, the invention also relates to a dimerization mixture of isobutene, wherein the ratio of the mass of the isobutene dimers to that of the isobutene trimers and tetramers is at least 2:1. The ratio is most preferably more than 4:1. Generally, no higher oligomers or polymers are found in a conventional product mixture.

The dimerization mixture in question according to the invention is preferably manufactured or it can be manufactured by means of the method described above.

As described above, prior art has used cation exchange resins, which comprise a styrene polymer, which is cross-linked with vinyl benzene, and any sulphonic acid groups adhering to the polymer, as a catalyst in the oligomerization of isobutene, the etherification of isobutene, and the decomposition of tertiary butyl ether. On the basis of prior art, the purpose of the present invention is to invent a new advantageous use for the cation exchange resins in question, in addition to the uses mentioned above.

This problem has now been solved by offering a use of the porous cation exchange resin, which is cross-linked with divinyl benzene and sulphonated, for reducing the oligomerization of isobutene in the dimerization of isobutene, and which is selected from a group including cation exchange resins, the portion of divinyl benzene units of which is 5% by weight at a minimum, and smaller than 20% by weight, and the acid capacity of which is 4.7 equivalents/kg at a minimum. According, the present invention uses a cation exchange resin, which is not a typical etherification catalyst such as Amberlyst 15 or Amberlyst 35.

In the use according to the present invention, the portion of divinyl benzene units of the cation exchange resin is preferably within 5–15% by weight, more preferably within 7–14% by weight, and most preferably within 10–12% by weight. The average diameter of the pores of the cation exchange resin is preferably 15 nm at a minimum and smaller than 30 nm, preferably about 20 to 25 nm.

In the following, examples are shown, the sole purpose of which is to illustrate the invention. The properties of the used catalysts appear from the following table.

| Catalyst | DVB[1] % | Sulfur % | Surface area[1], m2/g | Porosity[1], ml/g | Avg Pore diameter[1], nm | Concentr. of active sites[1], eq/kg | Particle size[1], mm |
|---|---|---|---|---|---|---|---|
| Catalyst 1 | 12 | 16.5[1] | 35 | 0.25 | 20 | 4.8 min | 0.6–0.85[3] |
| Catalyst 2 | 20 | 16[1] | 45 | 0.35 | 25 | 4.7 min | 0.6–0.85[3] |
| Catalyst 3 | 20 | 19.5[1] | 45 | 0.35 | 25 | 5.2 min | 0.7–0.95[3] |
| Catalyst 4 | 12 | 19.5[1] | 35 | 0.25 | 20 | 5.4 min | 0.6–0.8[3] |
| Catalyst 5 | >20 | 15.8[2] | 20–35 | 0.4–0.6 | 60–75 | 5.2 min | 0.4–1.2 |
| Catalyst 6 | >20 | 14.9[2] | 35 | 0.33 | 25 | 4.7 min | 0.4–0.65 |
| Catalyst 7 | 7 | 16.8[2] | 30 | NA | 25 | 5.0 min | NA |
| Catalyst 8 | 16 | 17.8[2] | NA | NA | NA | 5.18[4] | NA |
| Catalyst 9 | 10 | 20.7[2] | 24.6 | 0.15 | 24.5 | 5.72 | 0.75[3] |

[1]Reported by the manufacturer
[2]Defined in the laboratories of Fortum Oyj by means of a method that corresponds to the ASTM D5016-98 method. (Burning at 1350° C. + the NDIR detection of $SO_2$)
[3]Average particle size A detailed description of the dimerization and possible etherification process of isobutene is disclosed in publication FI 982250, page 8, and line 25—page 13, line 8, which is hereby enclosed in this application as a reference.

EXAMPLE 1

In the example, a mixture of isobutene/isopentane is dimerized as a semi batch mode in 35 ml ampoules at a temperature of 80° C. by means of various catalysts. The properties of the catalysts used in the comparison are shown in the appended table. The reaction mixture was replaced daily. Feed 1 was used to carry out two sets of tests, the one of which lasted 2 weeks, and the other one 5 weeks. The amount of dry catalyst per fresh feeding solution that was replaced daily was about 57 g/l. The composition of the Feed 1 used in the tests (in FIG. 1 2 week and 5 weeks) was as follows:

| Isobutene | 30% |
|---|---|
| N-butane | 1.2% |
| Isobutane | 3.2% |
| 1-butene | 0.1% |
| Isopentane | 59.9% |
| Tertiary butyl alcohol (TBA) | 0.5% |
| N-pentane | 5.1% |

Furthermore, a dimerization test of one day (in the figure 0 weeks) was conducted as a batch test by using the feed presented below:

| Isobutene | 36% |
|---|---|
| Isobutane | 60% |
| Tertiary butyl alcohol (TBA) | 4% |

The amount of dry catalyst per fresh feeding solution in Feed 2 was about 35 g/l. The polymer content was analysed by the $^{13}C$ CPMAS NMR method by comparing the spectra of the fresh and the used catalysts. The amount of polymer is calculated per dry catalyst. In the tests, the final conversion of the mixture was almost the same for all catalysts.

FIG. 1 shows the accumulation of polymer from the 2-week and 5-week dimerization tests and from the one-day test (0 week). The results indicate that the amount of polymer in Catalyst 1, which has the properties presented in the claims, is about half of the amount of polymer in the other catalysts in the 2-week and 5-week dimerization tests. In the short test (0 week), no polymer was observed in Catalyst 1.

| isobutene | 15% by weight |
|---|---|
| n-butane | 11% by weight |
| isobutane | 23.5% by weight |
| 1-butene | 14.5% by weight |
| cis-2-butene | 10.5% by weight |
| trans-2-butene | 15.5% by weight |
| tertiary butyl alcohol (TBA) | 1.3% by weight |
| sec-butanol | 0.7% by weight |
| other $C_2$–$C_6$ | 8.0% by weight |

EXAMPLE 2

Figure 2:
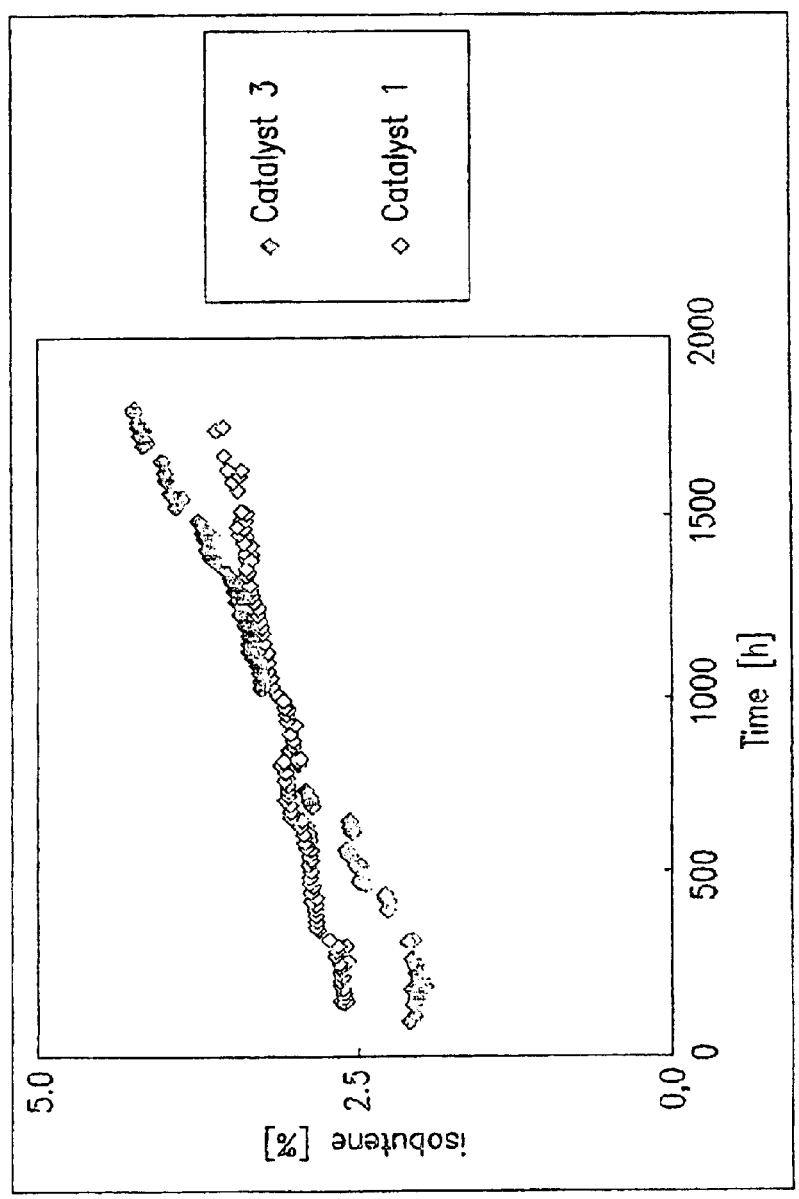
FIG. 2 shows an increase in isobutene content as a function time.

In the example, a typical refinery feed was dimerized continuously in a reactor tube, the composition being as follows:

The temperature was 82° C. Catalyst 3 and Catalyst 1 were used as catalysts. FIG. 2 presents the increase in the isobutene content at the output of the reactor as a function of time.

The results indicate that Catalyst 1, which has the said properties, maintains its activity for a considerably longer time than Catalyst 3, which has no said properties.

The results also indicate that because of the larger number of active sites of Catalyst 3, the isobutene reacts more at the beginning than with Catalyst 1. However, the loss of activity of Catalyst 3 already at about the 1000 th hour is so great that the conversion of Catalyst 1 is higher than that of Catalyst 3. As it is very important to achieve high conversion, the difference is significant.

EXAMPLE 3

In the example, a mixture of isobutene/isobutane was dimerized continuously in an isothermal reactor tube, where part of the reactor's product was recycled back to the reactor's feed. In this way, in addition to the isobutene, also its oligomers were obtained in the reactor's feed, whereby the deactivation of the catalyst was accelerated. In this way, it was possible to examine the deactivation in a shorter period of time.

The composition of the feed was as follows:
Isobutene 30% by weight
Isobutene 69% "
Hexane 0.5% "
Teriary butyl alcohol 0.5% "

Figure 3:
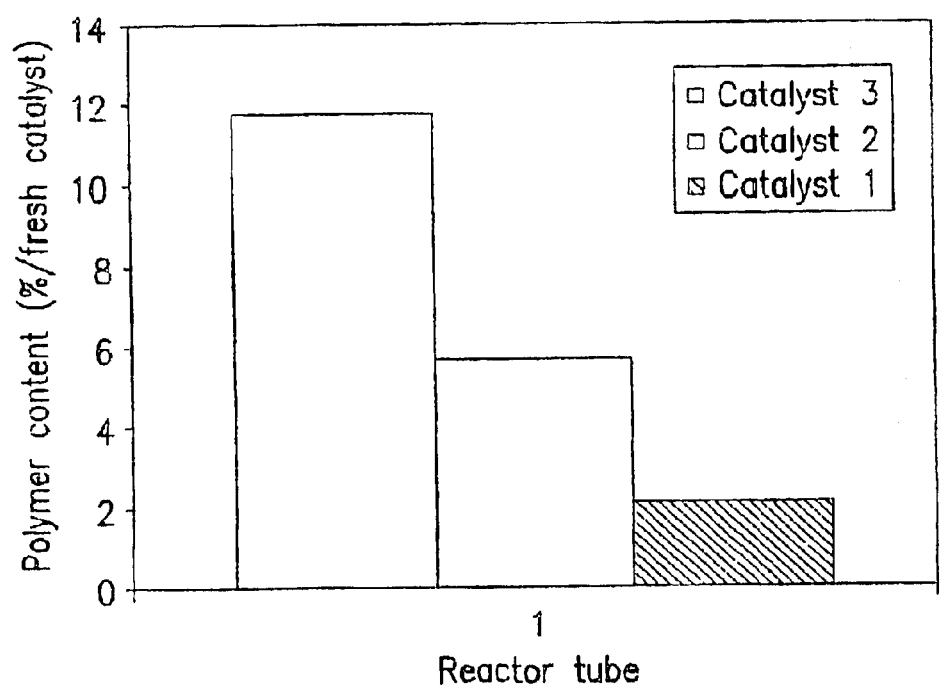
FIG. 3 shows the polymer contact as a function of the used catalyst.

The test was carried out using Catalyst 1, Catalyst 2, and Catalyst 3 at a temperature of 80° C. The duration of the test was 7 days. The polymer content was analysed by the $^{13}C$ CPMAS NMR method and calculated per dry catalyst. A catalyst sample was taken from the last part of the reactor. The results are shown in FIG. 3.

| Isobutene | 30% by weight |
|---|---|
| Isobutane | 69% by weight |
| Hexane | 0.5% by weight |
| Tertiary butyl alcohol | 0.5% by weight |

The results indicate that when using Catalyst 1, an amount corresponding to less than half of the polymer of Catalyst 2 and less than a fifth of the polymer of Catalyst 3 was accumulated. By comparing Catalyst 1 and Catalyst 2, we can see that cross-linking is a more significant factor in deactivation than the number of active sites of the catalyst. Catalysts 1 and 2 have almost the same number of active sites.

The results also show that the differences in the accumulation of polymer are not dependent on the test arrangements. Catalyst 1 both in the reactor tube and the CSTR reactor worked better than the other catalysts tested.

EXAMPLE 4

In the example, the same raffinate feed was dimerized in the reactor tube as in Example 2. There was no recycling in the reactor. The residence time (WHSV) in the test was about 10 l/h (as calculated from the mass of dry catalyst). The temperature was 60° C. The Oxygenate content (Tert-butyl alcohol+Sec-butyl alcohol) was 2.2% by weight. The catalysts used were Catalyst 1, Catalyst 4 of the same intermediate cross-linking, Catalysts 7 and 9 of a lower cross-linking, and Catalysts 3 and 8 of a high cross-linking.

At the beginning of the test, the conversion of isobutene+ 1-butene varied in accordance with the properties of the catalyst. Therefore, the conversion of isobutene and 1-butene is shown proportionally in the appended figure by dividing by the initial conversion. In addition, the divergence is balanced by adjusting the test results to a conversion curve. The initial conversions for the catalysts were as follows:

| Isobutene + 1-butene conversion | |
|---|---|
| Catalyst 1 | 10% by weight |
| Catalyst 3 | 14% by weight |
| Catalyst 4 | 13% by weight |
| Catalyst 7 | 9% by weight |
| Catalyst 8 | 14% by weight |
| Catalyst 9 | 15% by weight |

Figure 4:
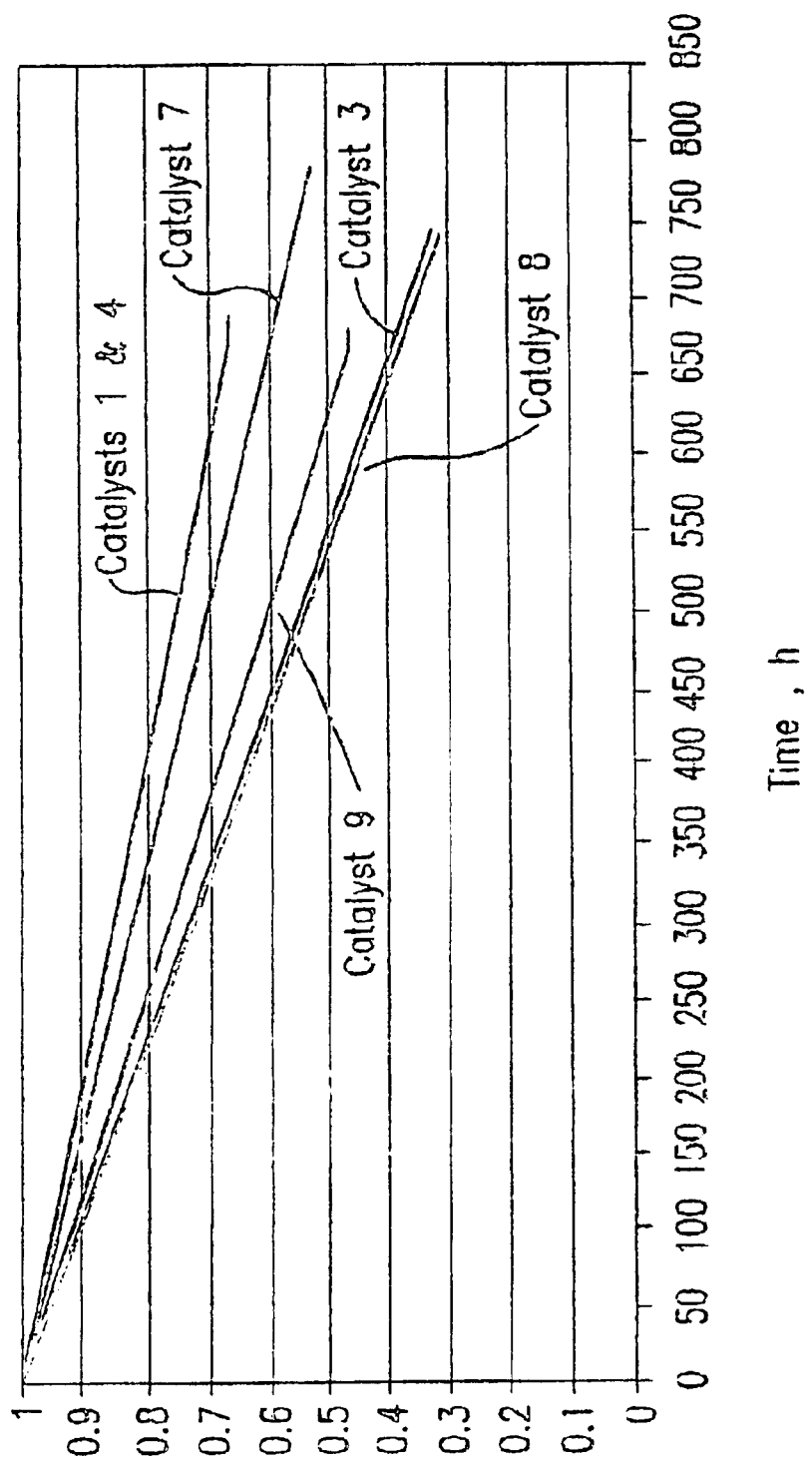
FIG. 4 shows a proportional reduction in conversion of the tested catalysts.

FIG. 4 shows that the proportional reduction in conversion is the lowest for Catalysts 1 and 4. The degrees of cross-linking are the same. The proportional reduction in conversion is similar for Catalysts 1 and 4, the degrees of cross-linking of which are the same. The next slowest reduction in conversion was that of Catalyst 7, the cross-linking of which was lower than that of Catalysts 1 and 4. The initial conversion of Catalyst 7 was low and similar to Catalyst 1. The third slowest proportional reduction in conversion was that of Catalyst 9, the cross-linking of which was lower than all other tested catalysts except Catalyst 7. Catalysts 3 and 8, catalysts of a high cross-linking, had the quickest reduction in conversion. On the basis of the test results, Catalysts 1 and 4 have properties, which are closest to the optimum.

What is claimed is:

1. A method for dimerizing isobutene, wherein, in dimerization conditions, the isobutene is brought into contact with a porous cation exchange resin, which comprises a styrene polymer cross-linked with divinyl benzene, and sulphonic acid groups adhering to the polymer, characterized in that the cation exchange resin, the acid capacity of which is 4.7 equivalents/kg at a minimum, and the portion of divinyl benzene units of which is within 7–14% by weight, and wherein the dimerization of isobutene is carried out in the presence of a substance containing oxygen.

2. A method according to claim 1, wherein the portion of divinyl benzene units is within 10–12% by weight.

3. A method according to claim 1, wherein the average diameter of the pores of the cation exchange resin is 15 nm at a minimum and smaller than 30 nm.

4. A method according to claim 1, wherein the porosity of the cation exchange resin is within 0.20–0.35 ml/g.

5. A method according to claim 1, wherein the amount of sulphur of the cation exchange resin is greater than 15% by weight and smaller than 21% by weight.

6. A method according to claim 1, wherein the specific surface area of the cation exchange resin is within 20–45 $m^2/g$.

7. A method according to claim 6, wherein the specific surface area of the cation exchange resin is about 35 $m^2/g$.

8. A method according to claim 1, wherein the average particle size of the cation exchange resin is within 0.6–0.85 mm.

9. A method according to claim 1, wherein the isobutene is in the form of a hydrocarbon mixture, the isobutene content of which is 10% by weight at a minimum.

10. A method according to claim 1, wherein the residence time of the feed with respect to the amount of catalyst (WHSV) is 0.1–200 $h^{1-}$.

11. A method according to claim 10, wherein the residence time (WHSV) is 0.2–20 $h^{1-}$.

12. A method according to claim 1, wherein the oxygen-containing substance is tertiary butyl alcohol.

13. A method according to claim 1, wherein the molar ratio between the tertiary butyl alcohol and the isobutene is smaller than 0.2.

14. A method according to claim 1, wherein the dimerization temperature of the isobutene is within about 40–120° C.

15. A method according to claim 1, wherein during the dimerization of isobutene, part of the isobutene is etherified by reacting the isobutene with a $C_1$–$C_4$ alcohol.

16. A method according to claim 15, wherein the $C_1$–$C_4$ alcohol is methanol.

17. A method according to claim 16, wherein the molar ratio between the methanol and the isobutene is 0.1–1.

18. A method according to claim 15, wherein the temperature of the combined dimerization and etherification of the isobutene is within 50–70° C.

19. A method according to claim 1, wherein the isobutene is dimerized by feeding the isobutene or a hydrocarbon mixture containing it first into reaction equipment for carrying out the dimerization, and then into distillation equipment for separating the dimer.

20. A method according to claim 1, wherein a dimerization is carried out by feeding the isobutene or a hydrocarbon mixture containing the isobutene into reaction and distillation equipment for carrying out the dimerization and for simultaneously separating the produced dimer by distillation.

* * * * *